(12) United States Patent
Wang et al.

(10) Patent No.: US 11,154,218 B2
(45) Date of Patent: Oct. 26, 2021

(54) FLOW SENSOR AND METHOD FOR PREVENTING CROSS-INFECTION AND APPLICATION THEREOF

(71) Applicant: ZHEJIANG E-LINKCARE MEDITECH CO., LTD, Taizhou (CN)

(72) Inventors: Tianxing Wang, Taizhou (CN); Xijiang Hu, Taizhou (CN); Zhimin Chen, Taizhou (CN); Lanfang Tang, Taizhou (CN); Jinling Liu, Taizhou (CN); Lei Wu, Taizhou (CN)

(73) Assignee: ZHEJIANG E-LINKCARE MEDITECH CO., LTD, Taizhou (CN)

(*) Notice: Subject to any disclaimer, the term of this patent is extended or adjusted under 35 U.S.C. 154(b) by 301 days.

(21) Appl. No.: 16/329,229

(22) PCT Filed: Aug. 28, 2017

(86) PCT No.: PCT/CN2017/099316
§ 371 (c)(1),
(2) Date: Feb. 28, 2019

(87) PCT Pub. No.: WO2018/041073
PCT Pub. Date: Mar. 8, 2018

(65) Prior Publication Data
US 2019/0246950 A1   Aug. 15, 2019

(30) Foreign Application Priority Data

Aug. 29, 2016 (CN) .......................... 201610747160.1
Aug. 17, 2017 (CN) .......................... 201710705110.1

(51) Int. Cl.
*A61B 5/087* (2006.01)
*A61B 5/091* (2006.01)
*G01F 1/44* (2006.01)

(52) U.S. Cl.
CPC .............. *A61B 5/087* (2013.01); *A61B 5/091* (2013.01); *G01F 1/44* (2013.01)

(58) Field of Classification Search
CPC ..... A61B 5/087–09; A61B 5/097; G01F 1/44; G01F 1/34–46
See application file for complete search history.

(56) References Cited

U.S. PATENT DOCUMENTS 5,134,890 A * 8/1992 Abrams ................. A61B 5/087
600/538
2013/0317379 A1 * 11/2013 Brimer ................... A61B 5/097
600/538

FOREIGN PATENT DOCUMENTS

| CN | 2367251 Y | 3/2000 |
| CN | 201160850 Y | 12/2008 |
| CN | 103070686 A | 5/2013 |

* cited by examiner

*Primary Examiner* — Thaddeus B Cox
(74) *Attorney, Agent, or Firm* — Bayramoglu Law Offices LLC

(57) ABSTRACT

A flow sensor for pulmonary function testing is provided, and the flow sensor is capable of preventing cross-infection and has a hollow tubular structure. The flow sensor includes a main breather tube and a pressure tapping hole arranged on a tube wall of the main breather tube. An outer wall of the main breather tube is provided with a pressure tapping stub in air communication with the pressure tapping hole. The volume of an inner cavity of the pressure tapping stub satisfies following condition: during the pulmonary function testing, air exhaled or inhaled by a tester enters the pressure tapping stub through the pressure tapping hole and is kept within the pressure tapping stub without contacting a connection pipeline outside of the flow sensor. The flow sensor can isolate contaminants, i.e., bacteria or viruses and prevent (Continued)

the contaminants from entering other connection pipelines or cavities of a pulmonary function instrument.

12 Claims, 4 Drawing Sheets

FLOW SENSOR AND METHOD FOR PREVENTING CROSS-INFECTION AND APPLICATION THEREOF

CROSS REFERENCE TO RELATED APPLICATIONS

This application is the national phase entry of International Application No. PCT/CN2017/099316, filed on Aug. 28, 2017, which is based upon and claims priority to Chinese Patent Application No. 201610747160.1, filed on Aug. 29, 2016, and Chinese Patent Application No. 201710705110.1, filed on Aug. 17, 2017, the entire contents of which are incorporated herein by reference.

TECHNICAL FIELD

The present invention disclosure relates to the field of pulmonary function testing, and more particularly, to a pulmonary function flow sensor for preventing cross-infection.

BACKGROUND

Products in the existing market such as pulmonary function instruments or pneumatometers use mouthpieces and disposable breathing filters to avoid cross-infection. Although the mouthpieces and the filters are disposable, filters having the best filter efficiency cannot be selected as the disposable breather filters. The higher the filter efficiency is, the better the isolation effect is, but the larger the resistance to the airflow, and the greater the effect on the gas flow measured during the pulmonary function testing, which increases the measurement error. Therefore, the disposable breather filters can only make allowance for the filter efficiency. Bacteria and viruses may be isolated by selecting filters having smaller airflow resistance, but it is impossible to completely isolate the bacteria or viruses from entering flow sensors.

To avoid cross-infection, after the pulmonary function instruments are used in the filters, the pulmonary function instruments may be cleaned and disinfected regularly. The medical pulmonary function instruments are expensive in price and complicated in structure. It is necessary for professionals to disassemble the instruments using special tools because they are damageable. It is needed to completely dry the pulmonary function instruments after disinfection and also it is needed to recalibrate the pulmonary function instruments before use, the whole process is cumbersome and consumes a lot of time and cost, and thus the instruments are out of commission for a long time.

SUMMARY

To overcome the above disadvantages, an objective of the present invention disclosure is to provide a flow sensor for pulmonary function testing able to prevent cross-infection, which has a hollow tubular structure. The flow sensor comprising a main breather tube and a pressure tapping hole arranged on a tube wall of the main breather tube. An outer wall of the main breather tube is provided with a pressure tapping stub in air communication with the pressure tapping hole. The volume of an inner cavity of the pressure tapping stub satisfies following condition: during the pulmonary function testing, air exhaled or inhaled by a tester enters the pressure tapping stub through the pressure tapping hole and is kept within the pressure tapping stub without contacting a connection pipeline outside of the flow sensor.

In accordance with an ideal gas state equation and Boyle's law, at a certain temperature, the volume of a certain amount of gas is inversely proportional to the pressure intensity of the gas. An appropriate pressure variation range is set, and the volume of the gas inhaled into or exhaled out of the inner cavity of the pressure tapping stub can be limited within the pressure tapping stub without contacting a connection pipeline outside of the flow sensor.

The volume of the inner cavity of the pressure tapping stub satisfies $V_1 > K(V_1 + V_2)$, such that the air exhaled or inhaled by the tester is kept within the pressure tapping stub without contacting the connection pipeline outside of the flow sensor, wherein $V_1$ represents an inner volume of the pressure tapping stub, $V_2$ represents a volume of air in a pressure conduit connecting the pressure tapping stub, and K represents a constant.

Further, a value of K is obtained based on Formula IV and by comparing an atmospheric pressure with $\Delta p$; the Formula IV is $$\Delta p = \frac{1}{2}\rho Q^2 \left(\frac{1}{A_2^2} - \frac{1}{A_1^2}\right),$$

wherein $\Delta p$ represents a differential pressure between an exhalation air inflow part and an apertura larynx part, $\rho$ represents a fluid density, Q represents a flow rate, $A_1$ represents a sectional area of the air inflow part, $A_2$ represents a sectional area of the apertura larynx part, and $\Delta p$ is obtained by regulating $A_1$ and $A_2$.

Preferably, the value of K is 10%.

Further, the main breather tube includes an exhalation air inflow part, a first pyramis, an apertura larynx part, and a second pyramis. A tube wall of the apertura larynx part is provided with a low-pressure pressure tapping hole and is communicated with the low-pressure pressure tapping hole. A tube wall of the exhalation air inflow part is provided with a first high-pressure pressure tapping hole and is communicated with a first high-pressure pressure tapping stub. The high-pressure pressure tapping stub is connected to a positive pressure terminal of a differential pressure transducer through a pressure conduit, and a low-pressure pressure tapping stub is connected to a negative pressure terminal of the differential pressure transducer through a pressure conduit.

Further, a tube wall of the second pyramis is provided with a second high-pressure pressure tapping hole and is communicated with a second high-pressure pressure tapping stub. The second high-pressure pressure tapping stub is connected to the positive pressure terminal of the differential pressure transducer.

Further, the exhalation air inflow part and the apertura larynx part are cylindrical, a diameter of the exhalation air inflow part is larger than that of the apertura larynx part, the first pyramis and the second pyramis are truncated cone-shaped, and one end of the first pyramis having a smaller diameter and one end of the second pyramis having a smaller diameter respectively face toward the apertura larynx part.

Further, an outer wall of a stub body of the pressure tapping stub is provided with a groove, into which a sealing ring is assembled.

Further, the flow sensor is also provided with a chucking device.

Further, the chucking device on the flow sensor can detachably connected to a pulmonary function instrument.

More further, the chucking device on the flow sensor is detachably connected to a pulmonary function instrument and is connected to the pressure conduit of the differential pressure transducer.

The present invention disclosure provides a method for preventing cross-infection during pulmonary function testing, in which a flow sensor is included. Having a hollow tubular structure, the flow sensor includes a main breather tube and a pressure tapping hole arranged on a tube wall of the main breather tube. An outer wall of the main breather tube is provided with a pressure tapping stub in air communication with the pressure tapping hole. The volume of an inner cavity of the pressure tapping stub satisfies following condition: during the pulmonary function testing, air exhaled or inhaled by a tester enters the pressure tapping stub through the pressure tapping hole and is kept within the pressure tapping stub without contacting a connection pipeline outside of the flow sensor.

The volume of the inner cavity of the pressure tapping stub satisfies following condition: $V_1 > K(V_1+V_2)$, wherein $V_1$ represents an inner volume of the pressure tapping stub, $V_2$ represents a volume of air in a pressure conduit connecting the pressure tapping stub, and K represents a constant.

Further, a value of K is obtained based on Formula IV and by comparing an atmospheric pressure with $\Delta p$; the Formula IV is $$\Delta p = \frac{1}{2}\rho Q^2 \left(\frac{1}{A_2^2} - \frac{1}{A_1^2}\right),$$

wherein $\Delta p$ represents a differential pressure between an exhalation air inflow part and an *apertura* larynx part, $\rho$ represents a fluid density, Q represents a flow rate, $A_1$ represents a sectional area of the air inflow part, $A_2$ represents a sectional area of the *apertura* larynx part, and $\Delta p$ is obtained by regulating $A_1$ and $A_2$.

Preferably, the value of K is 10%.

Further, the chucking device on the flow sensor can detachably connected to a pulmonary function instrument.

The present invention disclosure also provides a pulmonary function instrument for preventing cross-infection, which includes flow sensor. The flow sensor and a main body of the pulmonary function instrument are detachably assembled together to constitute the pulmonary function instrument. Having a hollow tubular structure, the flow sensor includes a main breather tube and a pressure tapping hole arranged on a tube wall of the main breather tube. An outer wall of the main breather tube is provided with a pressure tapping stub in air communication with the pressure tapping hole. The volume of an inner cavity of the pressure tapping stub satisfies following condition: during a pulmonary function testing, air exhaled or inhaled by a tester enters the pressure tapping stub through the pressure tapping hole and is kept within the pressure tapping stub without contacting a connection pipeline outside of the flow sensor.

The volume of the inner cavity of the pressure tapping stub satisfies following condition: $V_1 > K(V_1+V_2)$, wherein $V_1$ represents an inner volume of the pressure tapping stub, $V_2$ represents a volume of air in a pressure conduit connecting the pressure tapping stub, and K represents a constant. Preferably, the value of K is 10%.

Further, a value of K is obtained based on Formula IV and by comparing an atmospheric pressure with $\Delta p$; the Formula IV is $$\Delta p = \frac{1}{2}\rho Q^2 \left(\frac{1}{A_2^2} - \frac{1}{A_1^2}\right),$$

wherein $\Delta p$ represents a differential pressure between an exhalation air inflow part and an *apertura* larynx part, p represents a fluid density, Q represents a flow rate, $A_1$ represents a sectional area of the air inflow part, $A_2$ represents a sectional area of the *apertura* larynx part, and $\Delta p$ is obtained by regulating $A_1$ and $A_2$.

The pulmonary function instrument includes a differential pressure transducer. The differential pressure transducer is connected to the pressure tapping stub of the flow sensor through a pressure conduit.

Application of the flow sensor according to the present invention disclosure in a pulmonary function instrument.

Compared with the prior art, beneficial effects of the present invention disclosure are as below. Air in the pressure tapping stub of the flow sensor can play a role of isolation, such that gas exhaled by the tester cannot contact other instruments and equipment of the pulmonary function instrument, for example, a connecting base or a conduit connecting the pressure tapping stub. Therefore, the reusable connecting base and the conduit are impossible to contact the gas exhaled by the tester. Furthermore, the flow sensor according to the present invention disclosure can replaceable, and thus cross-infection can avoided.

DETAILED DESCRIPTION OF THE EMBODIMENTS

A flow sensor for pulmonary function detecting as shown in FIG. 1-FIG. 7 and a main body of a pulmonary function instrument are detachably assembled together to constitute the pulmonary function instrument. The flow sensor can prevent cross-infection, and includes a main breather tube and a pressure tapping hole arranged on a tube wall of the main breather tube, wherein an outer wall of the main breather tube is provided with a pressure tapping stub in air communication with the pressure tapping hole. A pulmonary function tester exhales or inhales air through the main breather tube. The pressure tapping hole serves as a sampling point where a differential pressure transducer collects flow rate of gas in the main breather tube. A gas-guide tube of the differential pressure transducer is not directly connected to the pressure tapping hole but is indirectly connected to the pressure tapping hole through a pressure tapping stub. A volume of an inner cavity of the pressure tapping stub satisfies following condition: during a pulmonary function testing, air exhaled or inhaled by a tester goes into/out of the pressure tapping stub through the pressure tapping hole, but the air is kept within the pressure tapping stub without contacting a connection pipeline outside of the flow sensor.

Embodiment 1 a flow sensor having two pressure tapping stubs

Figure 1:
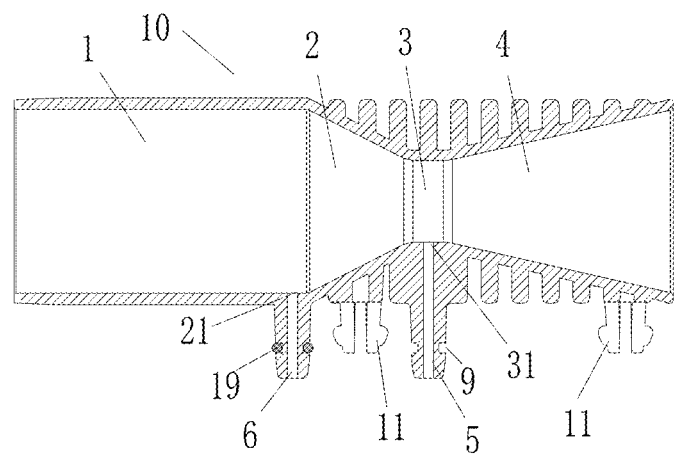
FIG. 1 is a schematic cross-sectional view of a disposable flow sensor having two pressure tapping stubs.
Figure 2:
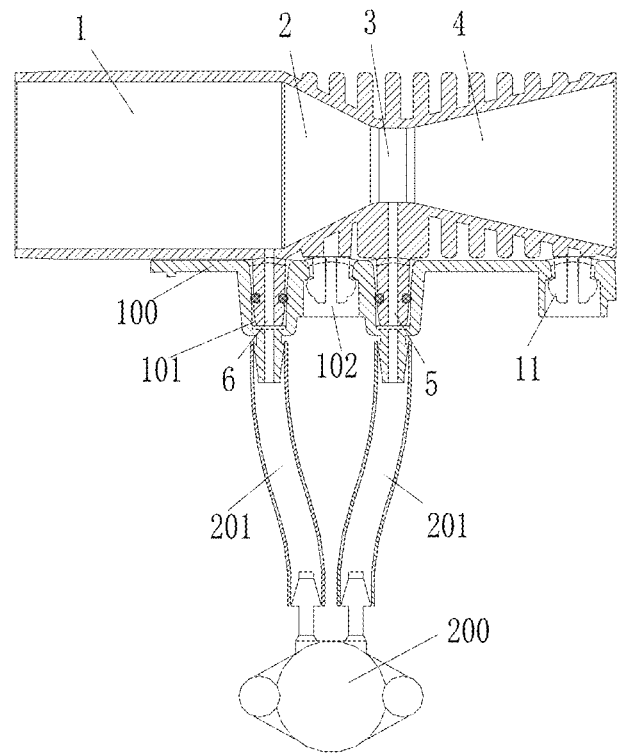
FIG. 2 is a schematic structural diagram of connecting the disposable flow sensor as shown in FIG. 1 to a differential pressure transducer.
Figure 3:
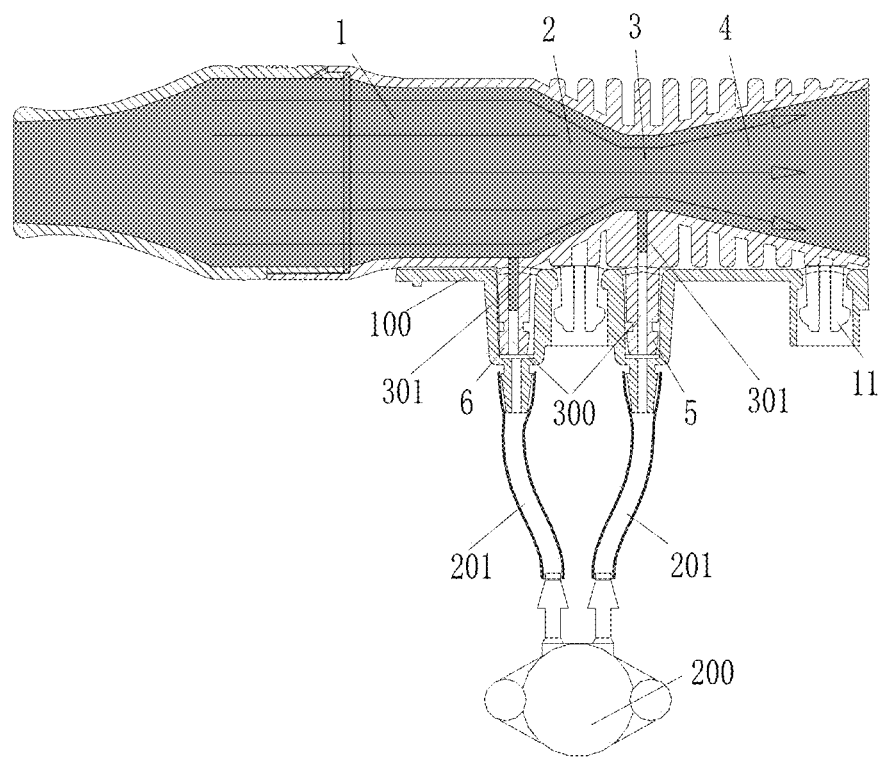
FIG. 3 is a schematic cross-sectional view of air column change location when exhaling via the disposable flow sensor having two pressure tapping stubs.
Figure 4:
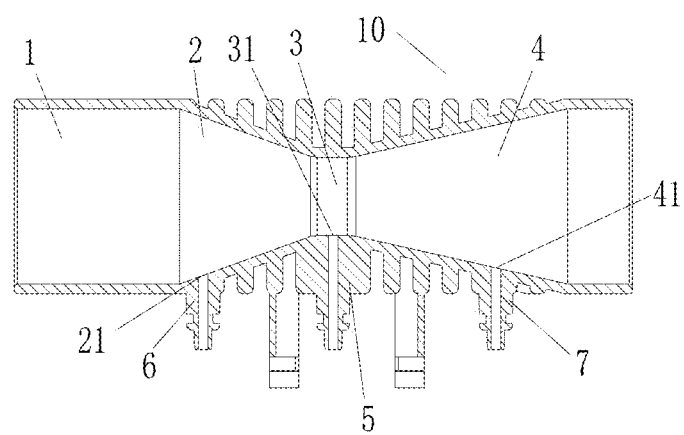
FIG. 4 is a schematic cross-sectional view of a disposable flow sensor having three pressure tapping stubs.

For the flow sensor as shown in FIG. 1-FIG. 3, its main breather tube includes an exhalation air inflow part 1, a first pyramis 2, an *apertura* larynx part 3 and a second pyramis 4 connected in sequence. A tube wall of the *apertura* larynx part 3 is provided with a low-pressure pressure tapping hole 31 and is communicated with a low-pressure pressure tapping stud 5. A tube wall of the exhalation air inflow part 1 is provided with a first high-pressure pressure tapping hole 21 and is communicated with a first high-pressure pressure tapping stub 6. The exhalation air inflow part 1 and the *apertura* larynx part 3 are cylindrical, and a diameter of the exhalation air inflow part is larger than that of the *apertura* larynx part. Sections of the first pyramis 2 and the second pyramis 4 are truncated cone-shaped, and one end of the first pyramis having a smaller diameter and one end of the second pyramis having a smaller diameter respectively face toward the *apertura* larynx part.

As shown in FIG. 2, a pressure conduit 201 of a differential pressure transducer 200 is connected to a pressure tapping hole 101 of a connecting base 100, and a location of the pressure tapping hole 101 corresponds to the low-pressure pressure tapping stud 5 and the first high-pressure pressure tapping stub 6 of the flow sensor. Connection between the pressure conduit of the differential pressure transducer and the pressure tapping hole of the flow sensor can be completed by inserting the pressure tapping stub of the flow sensor as shown in FIG. 2 into the pressure tapping hole 101 of the connecting base. The high-pressure pressure tapping stub is connected to a positive pressure terminal of the differential pressure transducer, and a low-pressure pressure tapping stub is connected to a negative pressure terminal of the differential pressure transducer. As shown in FIG. 3, after a tester inhales gas into the main breather tube of the flow sensor, the inhaled gas enters the low-pressure pressure tapping stud 5 and the high-pressure pressure tapping stub 6 respectively through the low-pressure pressure tapping hole 31 and the high-pressure pressure tapping hole 21. Thus, preexisting air 300 in the pressure tapping stub and the pressure conduit 201 is continuously compressed by the ingoing gas 301 until a new balance is established between gas inhaled into the pressure tapping stub and the preexisting gas. The volume of an inner cavity of the pressure tapping stub according to the present invention disclosure satisfies following condition: after gas exhaled by a tester enters the pressure tapping stub through the pressure tapping hole, the ingoing gas can compress the preexisting air in the pressure tapping stub and air in a pipeline connected to the pressure tapping stub, but an uppermost end of the compressed air always is within the pressure tapping stub. As shown in FIG. 3, the volume of the inner cavity of the pressure tapping stub is large enough to ensure that the ingoing gas 301 still remains in the pressure tapping stub instead of entering the pressure conduit when a new balance is established.

Embodiment 2 a flow sensor having three pressure tapping stubs

For the flow sensor as shown in FIG. 4-FIG. 7, its main breather tube includes an exhalation air inflow part 1, a first pyramis 2, an *apertura* larynx part 3 and a second pyramis 4 connected in sequence. A tube wall of the *apertura* larynx part 3 is provided with a low-pressure pressure tapping hole 31 and is communicated with a low-pressure pressure tapping stud 5. A tube wall of the first pyramis 2 is provided with a first high-pressure pressure tapping hole 21 and is communicated with a first high-pressure pressure tapping stub 6. A tube wall of the second pyramis 4 is provided with a second high-pressure pressure tapping hole 41 and is communicated with a second high-pressure pressure tapping stub 7. The exhalation air inflow part 1 and the *apertura* larynx part 3 are cylindrical, and a diameter of the exhalation air inflow part is larger than that of the *apertura* larynx part. Sections of the first pyramis 2 and the second pyramis 4 are truncated cone-shaped, and one end of the first pyramis having a smaller diameter and one end of the second pyramis having a smaller diameter respectively face toward the *apertura* larynx part.

Figure 5:
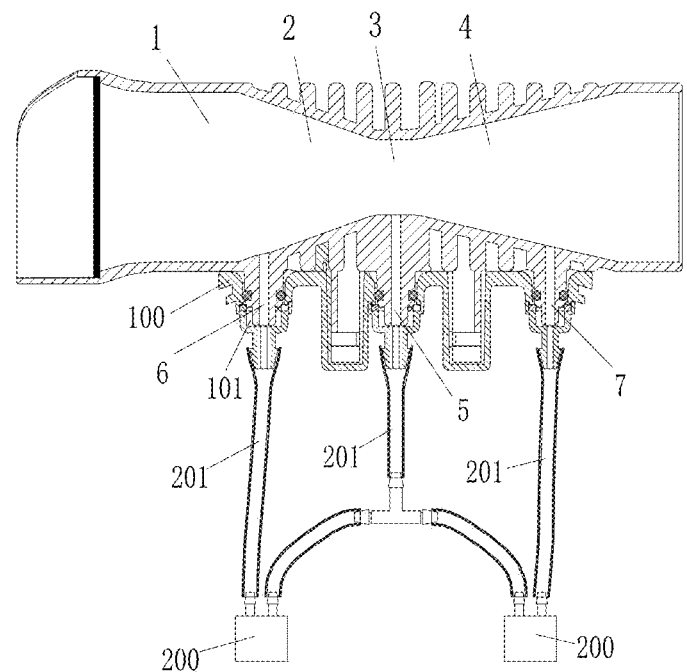
FIG. 5 is a schematic structural diagram of connecting the disposable flow sensor as shown in FIG. 4 to a differential pressure transducer.
Figure 6:
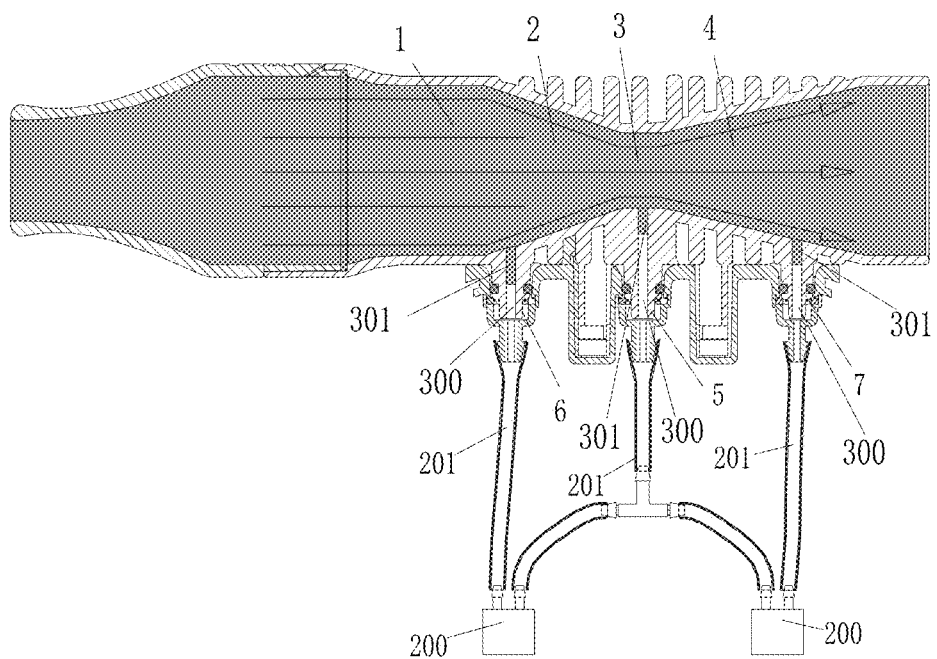
FIG. 6 is a schematic cross-sectional view of an air column change location when exhaling via the disposable flow sensor having three pressure tapping stubs.
Figure 7:
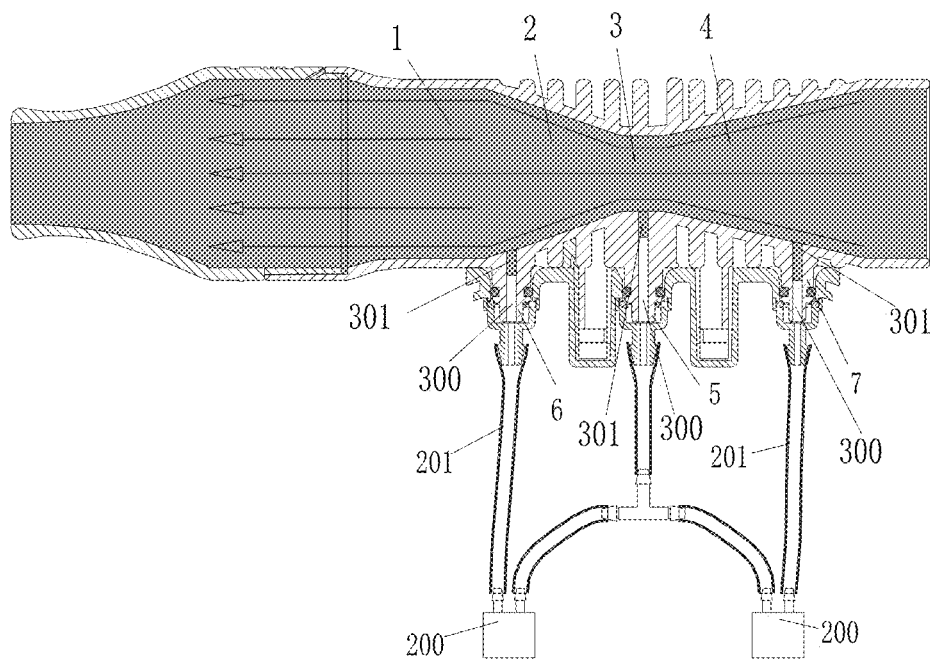
FIG. 7 is a schematic cross-sectional view of an air column change location when inhaling via the disposable flow sensor having three pressure tapping stubs.

As shown in FIG. 5, a pressure conduit 201 of a differential pressure transducer 200 is connected to a pressure tapping hole 101 of a connecting base 100, and a location of the pressure tapping hole 101 corresponds to the low-pressure pressure tapping stud and the high-pressure pressure tapping stub of the flow sensor. The first high-pressure pressure tapping stub 6 is connected to a positive pressure terminal of a first differential pressure transducer, a second high-pressure pressure tapping stub 7 is connected to a positive pressure terminal of a second differential pressure transducer, and low pressure terminals of the two pressure difference transducers are respectively connected to the low-pressure pressure tapping stud 5 through a three way pipe. As shown in FIG. 6, after the tester inhales gas into the main breather tube of the flow sensor, the inhaled gas enters the low-pressure pressure tapping stud 5 and the high-pressure pressure tapping stubs 6 and 7 respectively through the low-pressure pressure tapping hole 31 and the high-pressure pressure tapping holes 21 and 41. Thus, preexisting air 300 in the pressure tapping stub and the pressure conduit 201 is continuously compressed by the ingoing gas 301 until a new balance is established between gas inhaled into the pressure tapping stub and the preexisting gas. As shown in FIG. 7, after the tester inhales gas into the main breather tube of the flow sensor, the inhaled gas enters the low-pressure pressure tapping stud 5 and the high-pressure pressure tapping stubs 6 and 7 respectively through the low-pressure pressure tapping hole 31 and the high-pressure pressure tapping holes 21 and 41. Thus, preexisting air 300 in the pressure tapping stub and the pressure conduit 201 is continuously compressed by the ingoing gas 301 until a new balance is established between gas inhaled into the pressure tapping stub and the preexisting gas. The volume of an inner cavity of the pressure tapping stub according to the present invention disclosure satisfies following condition: after gas exhaled or inhaled by the tester enters the pressure tapping stub through the pressure tapping hole, the ingoing gas can compress the preexisting air in the pressure tapping stub and air in a pipeline connected to the pressure tapping stub, but an uppermost end of the compressed air always is within the pressure tapping stub. As shown in FIG. 6 and FIG. 7, the volume of the inner cavity of the pressure tapping stub is large enough to ensure that the ingoing gas 301 does not enter the pressure conduit when a new balance is established.

Embodiment 3 optimized structure of the flow sensor

When in use, the disposable flow sensor and the differential pressure transducer are detachably connected.

To ensure gas tightness of connection between the pressure conduit and the flow sensor in the testing process, a sealing element is arranged between the pressure tapping stub and a pipeline connected to the pressure tapping stub. For example, a groove 9 for placing a sealing ring 19 is arranged outside the pressure tapping stub of the flow sensor.

In some other embodiments, the flow sensor further includes a chucking device that can stably install the flow sensor on the main body of the pulmonary function instrument. The chucking device can prevent the flow sensor on the main body of the pulmonary function instrument from braking away therefrom. Meanwhile, after the use, the flow sensor can be drawn out of the main body of the pulmonary function instrument. The chucking device of the flow sensor includes, for example, but is not limited to a jaw 11 with a plum blossom-shaped structure which has certain elastic opening and closing. The connecting base or the main body of the flow sensor is provided with a component 102 mating with the jaw. For another example, the chucking device is an elastic buckle having a button structure.

Embodiment 4 method for calculating the volume of the inner cavity of the pressure tapping stub According to Bernoulli's principle, a fluid velocity and a pressure satisfy an equation: $p+\frac{1}{2}\rho v^{2}+\rho g h=C$, in which p represents a pressure intensity of the fluid at a certain point, v represents the flow velocity of the fluid at this point, ρ represents a density of the fluid, g represents an acceleration of gravity, h represents a height of this point, and C represents a constant. Gravity can neglected for gas, and thus the equation is simplified as Formula I: $p=C-\frac{1}{2}\rho v^{2}$, the greater the airflow velocity of the fluid is, the smaller the pressure is. The quantity of flow and the flow velocity satisfy Formula II: $v=Q/A$, in which Q represents the quantity of flow, and A represents the sectional area of a pipe where gas flows through this point. The quantity of flow of gas flowing through the exhalation air inflow part is equal to that of gas flowing through the *apertura* larynx part, but the sectional area of the exhalation air inflow part is not equal to that of the *apertura* larynx part, and thus the flow velocity of the exhalation air inflow part is not equal to that of the *apertura* larynx part according to Formula II. Supposing the sectional area of the exhalation air inflow part is $A_1$, the flow velocity thereof is $v_1$, and the pressure intensity is $p_1$; and the sectional area of the *apertura* larynx part is $A_2$, the flow velocity is $v_2$, and the pressure intensity is $p_2$. According to Formula I, it can derived that the differential pressure is $\Delta p=p_1-p_2=\frac{1}{2}\rho v_2^{2}-\frac{1}{2}\rho_1^{2}$, which is substituted into Formula II, such that Formula IV is obtained:

$$\Delta p = \frac{1}{2}\rho Q^2 \left( \frac{1}{A_2^2} - \frac{1}{A_1^2} \right).$$

According to testing standards of the pulmonary function instrument, it is detected that a peak flow is 14 L/s. A peak of the differential pressure between the exhalation air inflow part and the *apertura* larynx part is 10 kPa by regulating the sectional area of the exhalation air inflow part and the sectional area of the *apertura* larynx part. When no gas flows through the flow sensor, both $p_1$ and $p_2$ are standard atmospheric pressures. When gas flows through the flow sensor, both $p_1$ and $p_2$ fluctuate within the range of 10 kPa, the standard atmospheric pressure is about 101 kPa, and thus the variation range of the pressure intensity of the pressure tapping hole is 10%.

In accordance with an ideal gas state equation and Boyle's law, at a certain temperature, the volume of a certain amount of gas is inversely proportional to the pressure intensity of the gas, and Formula III is satisfied: $PV=C$, wherein P represents the pressure intensity of the gas, and V represents the volume of the gas. Supposing the inner volume of the pressure tapping stub is $V_1$ and the volume of gas in the pressure conduit is $V_2$, it can derived, according to Formula III, that P is inversely proportional to $(V_1+V_2)$. For example, $(V_1+V_2)$ is increased by 10% if P is decreased by 10%. Whereas $(V_1+V_2)$ is decreased by 10% if P is increased by 10%. Variation in size of the volume $(V_1+V_2)$ can cause fluctuations of the air column. However, airflow flowing through the flow sensor can partially inhaled into the pressure tapping stub instead of entering the pressure conduit as long as it is ensured $V_1>10\%(V_1+V_2)$. Since the flow sensor is disposable, air in the pressure tapping stub of the flow sensor can play a role of isolation, such that gas exhaled by the tester cannot contact the connecting base or the pressure conduit. Therefore, the reusable connecting base and the pressure conduit are impossible to contact the gas exhaled by the tester, and thus cross-infection can avoided.

Embodiment 5 contrast test for preventing cross-infection

Figure 8:
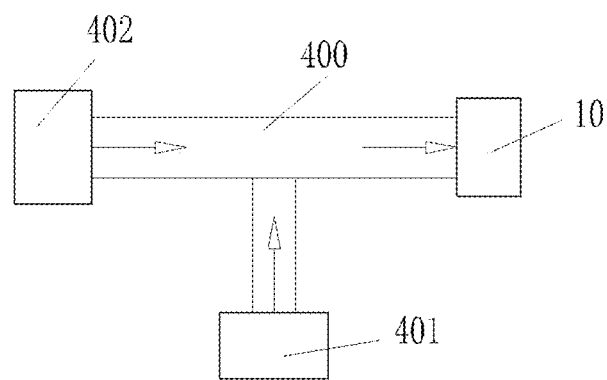
FIG. 8 is a schematic diagram of connecting the flow sensor in Embodiment 4 to a T-shaped pipe.

After sterilization treatment, a disposable flow sensor 10, a connecting base and a differential pressure transducer are respectively connected based on FIG. 2 (as an experimental group 1) and connected based on FIG. 5 (as an experimental group 2), and then are respectively connected to a nebulizer 401 and a 3 L calibration cylinder 402 through a T-shaped pipe 400, as shown in FIG. 8. 5 ml standard bacterial suspension having a bacterial colony of $5\times10^8$ cfu/ml is prepared using normal saline having a concentration of 0.9%, the nebulizer is started to generate bacterial aerosol mist particles, then it is simulated to exhale forcefully using the 3 L calibration cylinder to drive the bacterial aerosol mist particles and air into the flow sensor by continuously exhaling for five times, finally the disposable flow sensor is drawn out, and the connecting base is separated from the pressure conduit. Bacterination and bacterial culture are carried out respectively using sampling liquid, and colony counting is carried out after culturing bacteria for 48 hours. Reference is made to R&D OF BREATHING FILTER EXCLUSIVELY USED FOR PULMONARY FUNCTION DETECTING (master's thesis 2003, Guangzhou Medical University, May 2006) for specific contrast experiment steps.

TABLE 1 sterility test results of the experimental group 1

| The number of experiments | The number of colonies of the flow sensor (cfu/ml) | The number of colonies of the connecting base and the pressure conduit (cfu/ml) |
|---|---|---|
| 1 | $1.32 \times 10^5$ | 23 |
| 2 | $2.01 \times 10^5$ | 19 |
| 3 | $0.87 \times 10^5$ | 32 |
| 4 | $1.76 \times 10^5$ | 28 |
| 5 | $2.38 \times 10^5$ | 46 |

TABLE 2 sterility test results of the experimental group 2

| The number of experiments | The number of colonies of the flow sensor (cfu/ml) | The number of colonies of the connecting base and the pressure conduit (cfu/ml) |
| --- | --- | --- |
| 1 | 3.08 × 10⁵ | 34 |
| 2 | 1.93 × 10⁵ | 51 |
| 3 | 0.97 × 10⁵ | 26 |
| 4 | 4.27 × 10⁵ | 42 |
| 5 | 2.63 × 10⁵ | 37 |

Experimental results are seen in Table 1 and Table 2. The results show that the flow sensor as recited in the present invention disclosure can ensure that the connecting base and the pressure conduit connected to the flow sensor still meet sterile standards upon completion of the pulmonary function testing.

What is claimed is:

1. A flow sensor for preventing cross-infection, having a hollow tubular structure, and comprising a main breather tube and a pressure tapping hole arranged on a tube wall of the main breather tube, wherein an outer wall of the main breather tube is provided with a pressure tapping stub in air communication with the pressure tapping hole, wherein the pressure tapping stub is configured to connect with a pressure conduit of a differential pressure transducer, and a volume of an inner cavity of the pressure tapping stub satisfies the following condition: during a pulmonary function testing, air exhaled or inhaled by a tester enters the pressure tapping stub through the pressure tapping hole, and the air is kept within the pressure tapping stub without contacting the pressure conduit of the differential pressure transducer.

2. The flow sensor according to claim 1, wherein the volume of the inner cavity of the pressure tapping stub satisfies $V_1 > K(V_1 + V_2)$, wherein $V_1$ represents an inner volume of the pressure tapping stub, $V_2$ represents a volume of gas in the pressure conduit connecting with the pressure tapping stub, and K represents a constant.

3. The flow sensor according to claim 2, wherein the main breather tube includes an exhalation air inflow part and an *apertura* larynx part, a value of K is obtained based on a Formula IV and by comparing an atmospheric pressure with Δp obtained by calculating based on the Formula IV; the Formula IV is $$\Delta p = \frac{1}{2}\rho Q^2 \left( \frac{1}{A_2^2} - \frac{1}{A_1^2} \right);$$

wherein Δp represents a differential pressure between the exhalation air inflow part and the *apertura* larynx part, ρ represents a fluid density, Q represents a flow rate, $A_1$ represents a sectional area of the exhalation air inflow part, $A_2$ represents a sectional area of the *apertura* larynx part, and Δp is obtained by regulating $A_1$ and $A_2$.

4. The flow sensor according to claim 2, wherein a value of K is 0.1.

5. An application of a flow sensor in a pulmonary function instrument, comprising:
providing the flow sensor according to any one of claims 1-4,
assembling the flow sensor on a main body of the pulmonary function instrument to constitute the pulmonary function instrument.

6. The application according to claim 5, wherein the volume of the inner cavity of the pressure tapping stub satisfies V1>K(V1+V2), wherein V1 represents an inner volume of the pressure tapping stub, V2 represents a volume of gas in the pressure conduit connecting with the pressure tapping stub, and K represents a constant.

7. The application according to claim 6, wherein the main breather tube includes an exhalation air inflow part and an *apertura* larynx part, a value of K is obtained based on a Formula IV and by comparing an atmospheric pressure with Δp obtained by calculating based on the Formula IV; the Formula IV is $$\Delta p = \frac{1}{2}\rho Q^2 \left( \frac{1}{A_2^2} - \frac{1}{A_1^2} \right);$$

wherein Δp represents a differential pressure between the exhalation air inflow part and the *apertura* larynx part, ρ represents a fluid density, Q represents a flow rate, A1 represents a sectional area of the exhalation air inflow part, A2 represents a sectional area of the *apertura* larynx part, and Δp is obtained by regulating A1 and A2.

8. The application according to claim 6, wherein a value of K is 0.1.

9. A method for preventing cross-infection, comprising using a flow sensor having a hollow tubular structure to prevent the cross-infection; wherein the flow sensor comprises a main breather tube and a pressure tapping hole arranged on a tube wall of the main breather tube, an outer wall of the main breather tube is provided with a pressure tapping stub in air communication with the pressure tapping hole, wherein the pressure tapping stub is configured to connect with a pressure conduit of a differential pressure transducer, and a volume of an inner cavity of the pressure tapping stub satisfies the following condition: during a pulmonary function testing, air exhaled or inhaled by a tester enters the pressure tapping stub through the pressure tapping hole, and the air is kept within the pressure tapping stub without contacting the pressure conduit of the differential pressure transducer.

10. The method according to claim 9, wherein the volume of the inner cavity of the pressure tapping stub satisfies $V_1 > K(V_1 + V_2)$, such that the air exhaled or inhaled by the tester is kept within the pressure tapping stub without contacting the connection pipeline outside of the flow sensor, wherein $V_1$ represents an inner volume of the pressure tapping stub, $V_2$ represents a volume of gas in the pressure conduit connecting with the pressure tapping stub, and K represents a constant.

11. The method according to claim 10, wherein the main breather tube includes an exhalation air inflow part and an *apertura* larynx part, a value of K is obtained based on a Formula IV and by comparing an atmospheric pressure with Δp obtained by calculating based on the Formula IV; the Formula IV is $$\Delta p = \frac{1}{2}\rho Q^2 \left( \frac{1}{A_2^2} - \frac{1}{A_1^2} \right);$$

wherein Δp represents a differential pressure between the exhalation air inflow part and the *apertura* larynx part, ρ represents a fluid density, Q represents a flow rate, $A_1$ represents a sectional area of the exhalation air inflow part, $A_2$ represents a sectional area of the *apertura* larynx part, and Δp is obtained by regulating $A_1$ and $A_2$.

12. The method according to claim 10, wherein a value of K is 0.1.

* * * * *